United States Patent [19]

Greenlee et al.

[11] Patent Number: 5,451,579
[45] Date of Patent: Sep. 19, 1995

[54] 1-β-METHYL-CARBAPENEM, COMPOSITIONS CONTAINING SAME AND METHODS OF USE

[75] Inventors: Mark L. Greenlee, Rahway; Frank P. DiNinno, Old Bridge; Milton L. Hammond, Somerville, all of N.J.

[73] Assignee: Merck & Co., Inc., Rahway, N.J.

[21] Appl. No.: 196,749

[22] Filed: Feb. 15, 1994

[51] Int. Cl.$^6$ .................. A01N 43/00; A61K 31/395; C07D 487/00
[52] U.S. Cl. .................................... 514/210; 540/302
[58] Field of Search .......................... 540/302; 514/210

[56] References Cited

U.S. PATENT DOCUMENTS

| | | |
|---|---|---|
| 4,962,101 | 10/1990 | DiNinno et al. |
| 4,978,659 | 12/1990 | DiNinno et al. |
| 5,004,739 | 4/1991 | DiNinno et al. |
| 5,006,519 | 4/1991 | DiNinno et al. |
| 5,025,006 | 6/1991 | DiNinno et al. |
| 5,025,007 | 6/1991 | Greenlee et al. |
| 5,025,008 | 6/1991 | DiNinno et al. |
| 5,034,384 | 7/1991 | Greenlee et al. |
| 5,034,385 | 7/1991 | DiNinno et al. |
| 5,037,820 | 8/1991 | DiNinno et al. |
| 5,144,028 | 9/1992 | Greenlee et al. |
| 5,294,610 | 3/1994 | DiNinno et al. |

FOREIGN PATENT DOCUMENTS

0472306A1  2/1992  European Pat. Off.

*Primary Examiner*—Johann Richter
*Assistant Examiner*—Rebecca Cook
*Attorney, Agent, or Firm*—Richard C. Billups; Mark R. Daniel; Joseph F. DiPrima

[57] ABSTRACT

A carbapenem antibiotic of the formula I

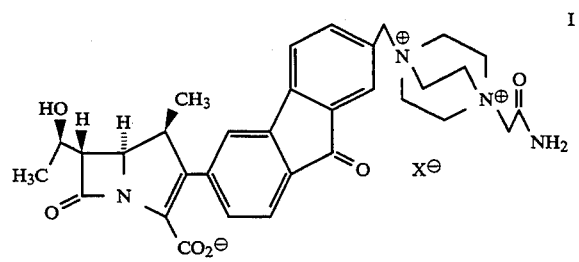

is disclosed. The variable $X^\ominus$ represents a counterion.

Pharmaceutical compositions and methods of use are also disclosed.

21 Claims, No Drawings

1-β-METHYL-CARBAPENEM, COMPOSITIONS CONTAINING SAME AND METHODS OF USE

BACKGROUND OF THE INVENTION

The present invention relates to an antibacterial agent of the 1-β-methyl-carbapenem class, in which the 2-position side-chain consists of a fluoren-9-on-3-yl group which is substituted by a (bis-quaternary ammonium)-methyl moiety.

U.S. Pat. No. 5,034,384 issued on Jul. 23, 1991 generally discloses 2-(fluoren-9-on-2-yl)- and 2-(fluoren-9-on-3-yl)-carbapenems as having anti-MRSA/MRCNS activity. Likewise, EP Publication No. 0 472 306 A 1 which was published on Feb. 26, 1992 discloses said 2-(fluoren-9-on-2-yl)- and 2-(fluoren-9-on-3-yl)-carbapenems.

The 2-(fluoren-9-on-3-yl)-carbapenem of the present invention is characterized by an antibacterial spectrum which is largely focused on gram-positive microorganisms, especially methicillin resistant *Staphylococcus aureus* (MRSA), methicillin resistant *Staphylococcus epidermidis* (MRSE), and methicillin resistant coagulase negative Staphylococci (MRCNS). Also, the present compound has safety and pharmacokinetic profiles which are superior to other compounds in the class.

There is an increasing need for agents which are effective against these pathogens (MRSA/MRCNS) and which are considered safe, i.e., relatively free from undesirable toxic side effects. The antibacterial compound of the present invention thus comprises an important contribution to therapy of these difficult to control pathogens.

SUMMARY OF THE INVENTION

The present invention provides a novel carbapenem compound of the formula:

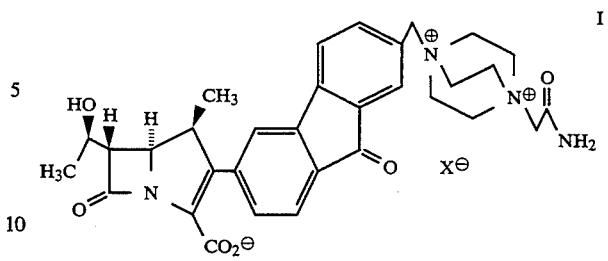

wherein $X^\ominus$ represents a negatively charged counterion.

A pharmaceutical composition is also included which is comprised of a compound represented by formula I in combination with a pharmaceutically acceptable carrier.

A method of treatment for a bacterial infection is also included, which is comprised of administering a compound represented by formula I to a mammalian patient in need of such treatment in an amount effective to treat the bacterial infection.

DETAILED DESCRIPTION

The starting materials for the syntheses described herein can be made according to the scientific and patent literature. For example, details pertaining to the formation of the 1-β-methyl-carbapenem nucleus and precursors thereto can be found in Shih, D. H., et al. *Heterocycles* 21:29 (1984) and in Fuentes, L. M. et al. *J. Am. Chem. Soc.*, 108, 4675 (1986). The syntheses are also disclosed in U.S. Pat. Nos. 4,269,772, 4,350,631, 4,383,946 and 4,414,155 and 4,994,568, all assigned to Merck and Co., Inc.

REACTION SCHEME A

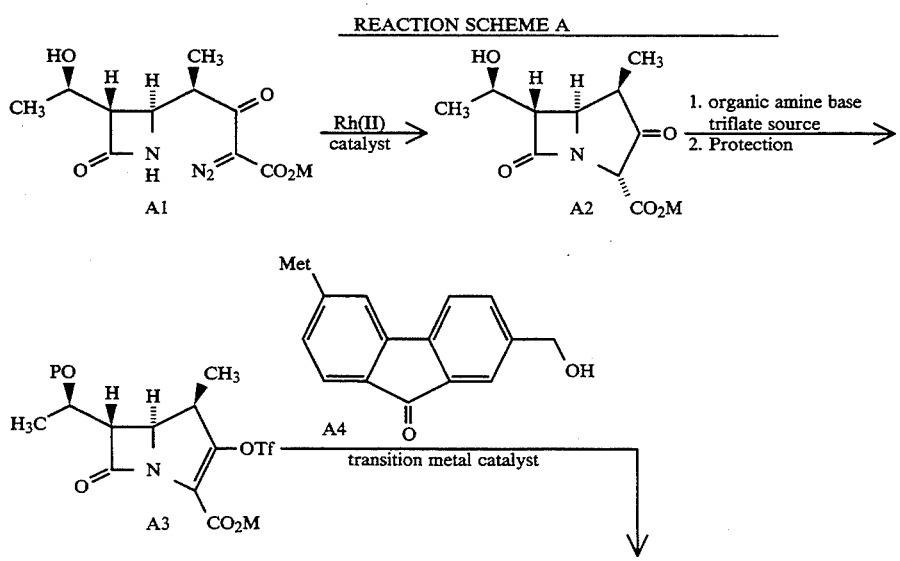

-continued
REACTION SCHEME A

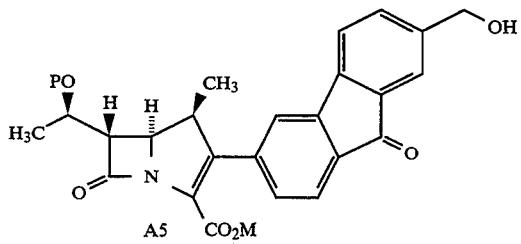

P = hydroxyl protecting group
M = carboxyl protecting group
Met = trialkyltin or boronic acid moeity
Tf = trifluoromethanesulfonyl Briefly, as shown in reaction scheme A, the diazo-β-ketoester A1 is cyclized to form the 1-β-methyl-2-oxocarbapenam A2, which is thereafter activated at the 2-position by conversion to the enol trifluoromethansulfonate derivative and protected in the hydroxyethyl side-chain to form A3. Intermediate A3 is then coupled with an appropriate fluorenone synthon A4 to produce the 1-β-methylcarbapenem intermediate A5.

The diazo-β-ketoester A1 is cyclized by heating at from about 15° C. to about 50° C. from about one to four hours in a suitable inert solvent such as dichloromethane, tetrahydrofuran or chloroform in the presence of a suitable transition metal catalyst such as rhodium(II) octanoate [$Rh_2(Oct)_4$] or rhodium(II) acetate [$Rh_2(OAc)_4$] to provide the 1-β-methyl-2-oxocarbapenam A2.

The intermediate A2 can be reacted in situ with a suitable organic nitrogen base such as triethylamine, diisopropylethylamine, diisopropylamine and the like, followed by a suitable trifluoromethanesulfonylating agent such as trifluoromethanesulfonic anhydride, trifluoromethanesulfonyl chloride and the like, at reduced temperature such as from about −78° C. to −20° C. for about five to forty-five minutes. The hydroxyethyl side-chain of the resulting enol trifluoromethansulfonate intermediate can then be protected by introduction of an appropriate protecting group. For example, a suitable organic nitrogen base such as triethylamine, diisopropylethylamine, diisopropylamine or the like is then added to the reaction solution followed by a silylating agent such as triethylsilyl or trimethylsilyl trifluoromethanesulfonate to provide, after a reaction period of about five minutes to about two hours, the trifluoromethanesulfonate intermediate A3. The activated 2-(trifluoromethanesulfonyloxy)carbapenem intermediate A3 is thereafter coupled with an appropriately substituted fluoren-9-one A4 as described further below.

The synthesis of the fluoren-9-one A4 can be varied depending upon the value of Met. When Met represents a trialkyltin moiety, the fluoren-9-one is synthesized according to the process described in U.S. patent application Ser. No. 485,096 filed Feb. 26, 1990, and in U.S. Pat. No. 5,034,384 issued on Jul. 23, 1991. Briefly, 6-bromo-2-hydroxymethylfluoren-9-one is reacted with hexamethylditin, tetrakis(triphenyl-phosphine)palladium(O) and triphenylphosphine in toluene at about 110° C. to produce 6-trimethylstannyl-2-hydroxymethylfluoren-9-one. An aprotic polar coordinating solvent, such as N,N-dimethylformamide, 1-methyl-2-pyrrolidinone and the like, can also be added.

When Met represents a boronic acid moiety, the fluoren-9-one is synthesized according to U.S. patent application Ser. No. 978,598 filed on Nov. 19, 1992 and copending herewith. Briefly, 3-bromo-9,9-dimethoxy-7-methoxymethylfluorene is reacted with n-butyllithium and the metalated fluorene is boronated with triisopropyl borate [$B(Oi-Pr)_3$]. After hydrolysis and removal of protecting groups, 2-hydroxymethylfluoren-9-one-6-boronic acid is obtained.

The conditions of the coupling reaction between the activated carbapenem A3 and the fluorenone A4 vary depending upon the value of Met. When Met is a trialkyltin moiety, a solution of 2-(trifluoromethanesulfonyloxy)carbapenem A3 in a suitable solvent such as tetrahydrofuran, 1-methyl-2-pyrrolidinone, N,N-dimethylformamide or dichloromethane is combined with a palladium compound, e.g., tris(dibenzylideneacetone)-dipalladium-chloroform, bis(dibenzylideneacetone)palladium, palladium acetate, bis(acetonitrile)palladium(II) chloride and the like, optionally a suitably substituted phenylphosphine, such as tris(4-methoxyphenyl)phosphine, tris(2,4,6-trimethoxyphenyl)phosphine and the like, and the trialkylstannyl-fluorenone A4. A metal halide, such as lithium chloride, zinc chloride and the like or an ammonium halide such as tetraethylammonium chloride, diisopropylammonium hydrochloride and the like, is added and the reaction solution is maintained at a suitable temperature, such as from about 0° C. to 50° C., and allowed to stir for a suitable amount of time such as from a few minutes to about 48 hours. The carbapenem A5 is thereafter obtained by conventional isolation/purification methodology known in the art.

When Met is a boronic acid moiety, the carbapenem A3 and 2-hydroxymethylfluoren-9-one-6-boronic acid A4 are combined in a coupling solvent with a coupling base and a transition metal catalyst as described in U.S. application Ser. No. 978,598.

Coupling bases for purposes of this reaction include metal hydroxides, metal $C_{1-4}$ alkoxides and metal carbonates. Examples of metal hydroxides include barium, potassium, sodium, lithium and thallium hydroxide. Examples of metal alkoxides include sodium, potassium and lithium t-butoxide. Examples of metal carbonates include potassium and sodium carbonate.

Coupling solvents for purposes of this reaction include di-$C_{1-3}$ alkyl formamides, di-$C_{1-3}$ alkyl sulfoxides, N-alkylpyrrolidinones, halocarbons, ethers, aromatic and aliphatic solvents. An example of a di-$C_{1-3}$ alkyl formamide is N,N-dimethylformamide. An example of a di-$C_{1-3}$ alkyl sulfoxide is dimethylsulfoxide. Examples of N-alkylpyrrolidones include N-methylpyrrolidone and N-ethylpyrrolidone. An example of a halocarbon is dichloromethane. Examples of ethereal solvents include diethyl ether, di-n-butyl ether, tetrahydropyran and tetrahydrofuran. Examples of aromatic solvents include benzene, toluene and xylene. Examples of aliphatic solvents include n-hexane and cyclohexane.

Transition metal catalysts for purposes of this reaction include palladium and nickel catalysts. Examples of palladium catalysts include Pd(O) and Pd(II) catalysts. The Pd(O) catalysts include tris(dibenzylideneacetone)-dipalladium-chloroform, tris(dibenzylideneacetone)-dipalladium and bis(dibenzylideneacetone)palladium. Examples of Pd(II) catalysts include $Pd(OAc)_2$ and $PdCl_2$.

The boronic acid derivative A4 is added as a solution in a suitable polar solvent such as 1-methyl-2-pyrrolidinone, N,N-dimethylformamide or tetrahydrofuran to a solution of 2-(trifluoromethanesulfonyloxy)carbapenem A3 in a suitable solvent such as 1-methyl-2-pyrrolidinone, N,N-dimethylformamide, tetrahydrofuran or dichloromethane followed by the addition of a palladium compound such as tris(dibenzylideneacetone)dipalladium-chloroform, bis(dibenzylideneacetone)palladium, palladium acetate, bis(acetonitrile)palladium(II) chloride and the like, optionally a phosphine such as triphenylphosphine, and an inorganic base such as aqueous potassium hydroxide, aqueous potassium carbonate, aqueous cesium hydroxide, or solid potassium carbonate. The reaction solution is maintained at a suitable temperature, such as from about 0° C. to 60° C., and allowed to stir for a suitable amount of time such as from a few minutes to 48 hours. The carbapenem A5 is then obtained by conventional isolation/purification methodology known in the art.

While the intermediates A2 and A3 may be isolated by conventional means, it is preferable to carry-out the entire sequence of reaction scheme A in situ.

Conversion of the carbapenem intermediate A5 into the final compound may be accomplished as shown in reaction scheme B. Briefly, the hydroxyl group of A5 is convened into a suitable leaving group, Z, which is thereafter displaced with 1-(aminocarbonylmethyl)-4-aza-1-azoniabicyclo(2.2.2)octane trifluoromethanesulfonate B2 to provide B3. The protecting groups are removed from B3 in conventional fashion and then the desired counterion $X^-$ is introduced to provide compound I.

The following are examples of suitable leaving groups Z: alkyl and substituted alkylsulfonates, aryl and substituted arylsulfonates and halides. The common sulfonate leaving groups are: methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy and p-nitrobenzenesulfonyloxy. The preferred halogen leaving groups are bromide and iodide.

Referring to reaction scheme B, the hydroxyl group of A5 may be convened into a suitable alkyl- or arylsulfonate leaving group by treating with an appropriate agent such as an alkyl- or arylsulfonyl chloride or an alkyl- or arylsulfonic anhydride in the presence of a hindered organic base such as triethylamine. A suitable solvent such as dichloromethane is employed and the reaction is carded out at reduced temperature, such as from about −70° C. to 0° C.

REACTION SCHEME B

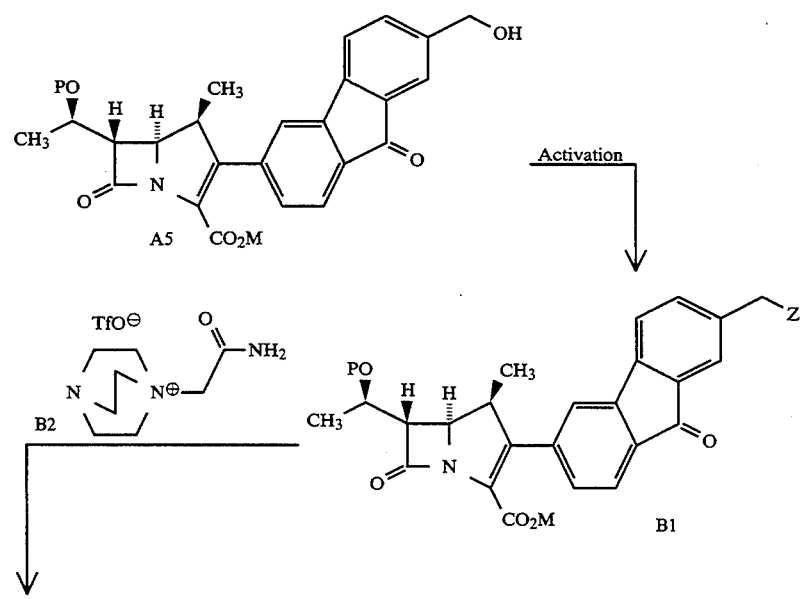

REACTION SCHEME B

-continued

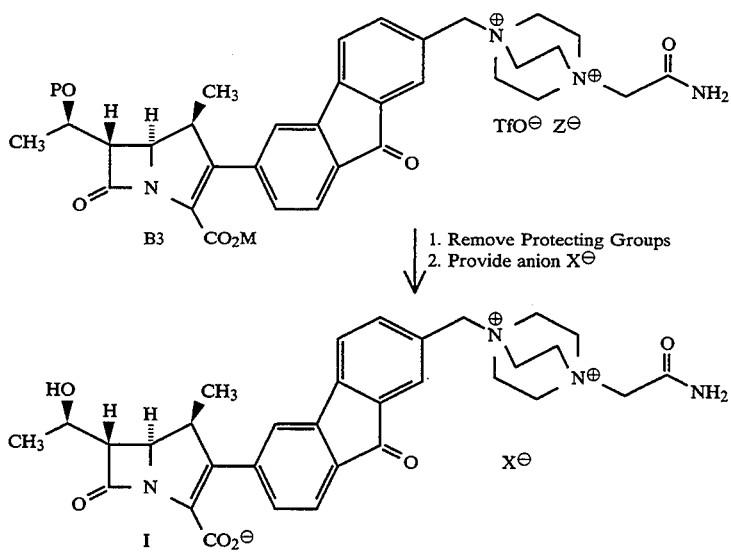

The preferred halogen leaving groups may be introduced by displacing an alkyl- or arylsulfonate leaving group with an appropriate metal halide. Thus, compound B1, where Z is an alkyl- or arylsulfonate group, is reacted with a suitable metal halide such as sodium iodide or s potassium bromide in a suitable solvent such as acetone, acetonitrile, tetrahydrofuran, 1-methyl-2-pyrrolidinone and the like, at from about 0° C. to 50° C. Alternatively, the hydroxyl group of A5 may be directly converted into an iodide group by reaction with an appropriate reagent, e.g. by treatment of A5 with methyl triphenoxyphosphonium iodide in a suitable solvent, such as N,N-dimethylformamide, at reduced or ambient temperatures.

Introduction of the cationic substituent is accomplished by reacting B1 with 1 -(aminocarbonylmethyl)-4-aza- 1-azoniabicyclo(2.2.2)octane trifluoromethanesulfonate B2 in a suitable solvent, such as acetonitrile, tetrahydrofuran, 1-methyl-2-pyrrolidinone and the like, at about 0° C. to 50° C. to provide B3. When the leaving group, Z, is iodide or bromide, this displacement reaction may also be facilitated by the addition of silver trifluoromethanesulfonate to the reaction mixture.

When the reactive trifluoromethanesulfonate group is employed as the leaving group Z in B1, the activation and displacement steps must be carded-out in situ, since in this case B1 cannot be isolated by conventional techniques due to its instability. Thus, treatment of A5 with a slight excess of trifluoromethanesulfonic anhydride in the presence of a hindered, non-nucleophilic base such as 2,6-lutidine, 2,4,6-collidine, or 2,6-di-tert-butyl-4-methyl-pyridine in a suitable solvent, such as dichloromethane or acetonitrile, at from about −78° C. to −20° C. provides for the generation of the trifluoromethanesulfonate activating group. Introduction of the bis-quaternary ammonium group is then accomplished by reacting the above trifluoromethanesulfonate intermediate in situ with B2 at reduced temperature.

The amine B2 is prepared by reaction of 1,4-diazabicyclo[2.2.2]octane with one equivalent of an appropriate alkylating agent, such as $H_2NC(O)CH_2Br$, $H_2NC(O)CH_2Cl$, or $H_2NC(O)CH_2I$ in an appropriate solvent such as acetonitrile, tetrahydrofuran or 1-methyl-2-pyrrolidinone. The halide counterion is then replaced with a trifluoromethanesulfonate counterion by reaction with a trifluoromethanesulfonate salt such as silver or sodium trifluoromethanesulfonate in an appropriate solvent such as acetonitrile, methanol or water. Alternatively, the alkylation may be carried out in the presence of about one equivalent of silver trifluoromethanesulfonate which generates the desired trifluoromethanesulfonate salt B2 directly.

In the preparation methods described herein, the carboxyl group at the 3-position and the hydroxyl group at the 8-position of the carbapenem typically remain blocked until the final product is prepared. These blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with fluoride ion, treatment with a transition metal catalyst and a nucleophile, and catalytic hydrogenation.

Examples of suitable hydroxyl protecting groups are: t-butylmethoxyphenylsilyl, t-butoxydiphenylsilyl, trimethylsilyl, triethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Preferred hydroxyl protecting groups are trimethylsilyl and triethylsilyl.

Examples of suitable carboxyl protecting groups are: benzhydryl, o-nitrobenzyl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, p-methoxyphenyl, 4-pyridylmethyl and t-butyl. A preferred carboxyl protecting group is p-nitrobenzyl.

Many other suitable hydroxyl and carboxyl protecting groups are known in the an. See, e.g., T. W. Greene, *Protective Groups in Organic Synthesis*, John Wiley & Sons, Inc., 1981 (Chapters 2 and 5).

Removal of the protecting groups of B3 where P is triethylsilyl and M is p-nitrobenzyl is accomplished by exposing B3 to aqueous acidic conditions, such as dilute hydrochloric acid, in an organic solvent such as tetrahydrofuran at from 0° C. to 30° C. for a few minutes to several hours. The resulting desilylated carbapenem may be isolated by conventional techniques, but is more conveniently taken directly into the final deprotection process. Thus, the reaction mixture is neutralized by addition of an inorganic base such as sodium bicarbonate or sodium hydroxide and optionally a pH 6.5 to pH 7.0 aqueous buffer such as 4-morpholinepropanesulfonic acid/NaOH (MOPS) or $NaH_2PO_4/Na_2HPO_4$. The reaction mixture is then hydrogenated at or slightly above atmospheric pressure over a heterogeneous catalyst such as rhodium on carbon, rhodium on alumina, palladium on carbon or the like at from 0° C. to 30° C. for from 30 minutes to 6 hours to remove the p-nitrobenzyl ester protecting group.

After the protecting groups are removed from B3, the desired counterion X- may be introduced by standard techniques, e.g. by employing an anion exchange resin or by utilizing the principle of mass action, i.e. exposure of compound to a large excess of the desired anion. For example, introduction of the chloride counterion may be accomplished by dissolving compound in a solution containing a large excess of sodium chloride. The final compound I where $X^-=Cl^-$ is then isolated by conventional techniques.

Reaction scheme C illustrates an alternative method for s introduction of the 1,4-diazoniabicyclo[2.2.2]octanyl group. Briefly, the hydroxyl group of A5 is convened into a suitable leaving group, Z, as described in reaction scheme B giving B1. Reaction of B1 with with 1,4-diazabicyclo[2.2.2]octane provides C1 which is alkylated with an appropriate reagent $H_2NC(O)CH_2Y$ to give C2. It is recognized that depending on the identity of the counterions $Z^-$ and $Y^-$, C2 may be the same as B3. Removal of the protecting groups from C2 and introduction of the desired counterion $X^-$ as described above for reaction scheme B provides the final compound I.

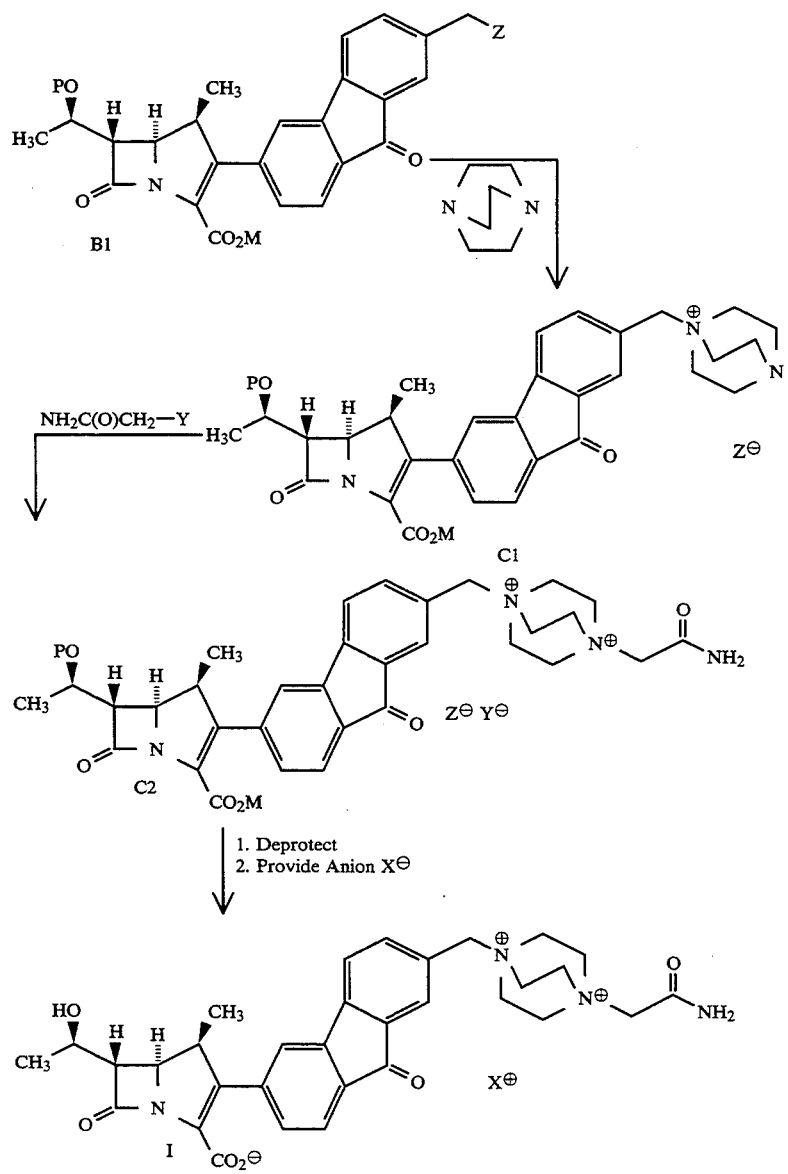

REACTION SCHEME C

Referring to reaction scheme C, introduction of the cationic substituent is accomplished by reacting B1 with 1,4-diazabicyclo[2.2.2]octane in a suitable solvent, such as acetonitrile, tetrahydrofuran, 1-methyl-2-pyrrolidinone dichloromethane and the like, at about 0° C. to 50° C. to provide C1. When the leaving group, Z, is iodide or bromide, this displacement reaction may also be facilitated by the addition of silver trifluoromethanesulfonate to the reaction mixture.

When the leaving group, Z, in B1 is trifluoromethanesulfonate, the activation and displacement steps must be carried-out in situ, since in this case B1 cannot be isolated by conventional techniques due to its instability. Thus, treatment of A5 with a slight excess of trifluoromethanesulfonic anhydride in the presence of a hindered, non-nucleophilic base such as 2,6-lutidine, 2,4,6-collidine, or 2,6-di-tert-butyl-4-methyl-pyridine in a suitable solvent, such as dichloromethane or acetonitrile, at from about −78° C. to −20° C. provides for the generation of the trifluoromethanesulfonate activating group. Introduction of the 4-aza-1-azoniabicyclo(2.2.2)octanyl group is then accomplished by reacting the trifluoromethanesulfonate intermediate in situ with 1,4-diazabicyclo[2.2.2]octane at reduced temperature such as from about −78° C. to 0° C. to provide intermediate C1.

It is also possible to use the reacting amine as the base for the formation of the trifluoromethanesulfonate activating group. In this case, treatment of A5 with trifluoromethanesulfonic anhydride in the presence of at least two equivalents of 1,4-diazabicyclo[2.2.2]octane at reduced temperature such as from −78° C. to 0° C. provides intermediate C1.

Compound C1 is reacted with a desired alkylating agent $H_2NC(O)CH_2Y$, such as $H_2NC(O)CH_2Br$, $H_2NC(O)CH_2Cl$, or $H_2NC(O)CH_2I$, in a suitable solvent such as acetonitrile, tetrahydrofuran, 1-methyl-2-pyrrolidinone and the like at from about 0° C. to 50° C., optionally in the presence of silver trifluoromethanesulfonate, to provide C2.

Removal of the protecting groups from C2 and introduction of the desired counterion $X^-$ as described above for reaction scheme B provides the final compound.

The compounds shown in the reaction schemes are electronically balanced. Since a bis-quaternary ammonium group is present in B3, two negatively charged counterions are also present to provide overall electronic balance. One of these counterions is trifluoromethanesulfonate which derives from B2. The other counterion, $Z^-$, varies depending on which activating group Z is employed. When a halogen activating group Z is used in B1 and the displacement with B2 is carried out in the presence of silver trifluoromethanesulfonate, then $Z^-$ is normally trifluoromethanesulfonate. Likewise, the counterion $Z^-$ in C1 and C2 varies depending on which activating group Z is employed in B1. The counterion $Y^-$ in C2 varies according to the alkylating agent $H_2NC(O)CH_2Y$ that is used. In the final compound I, the charge of the bis-quaternary ammonium group is balanced by a negatively charged counterion, $X^-$, in conjunction with the negatively charged carboxylate, $CO_2^-$, which is contained in the molecule. Counterion $X^-$ is a pharmaceutically acceptable anionic species and may differ from $Z^-$ and $Y^-$. The desired counterion $X^-$ may be introduced by standard techniques as described above. It is understood that when the counterion $X^-$ is an anionic species possessing more than one negative charge, then an appropriate amount of $X^-$ is present to result in overall electronic balance in the final compound. For example, when $X^-$ is a dianionic species, then one-half of a molar equivalent of $X^-$ is present relative to the carbapenem moiety. Suitable negatively charged counterions, $X^-$, are listed below under the description of pharmaceutically acceptable salts.

The carbapenem compound of the present invention is useful in various pharmaceutically acceptable salt forms for the treatment of bacterial infections in animal and human subjects. The term "pharmaceutically acceptable salt" refers to those salt forms which would be apparent to the pharmaceutical chemist. i.e., those which are substantially non-toxic and which provide the desired pharmacokinetic properties, palatability, absorption, distribution, metabolism or excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is concerned with pharmaceutical compositioris and methods of treating bacterial infections utilizing the carbapenem compound of formula I.

The pharmaceutically acceptable salt forms of the carbapenem compound of formula I mentioned above refer to the various possibilities for the charge balancing counterion $X^-$. Anions derived from inorganic or organic acids are suitable. Representative examples of such counterions are the following: acetate, adipate, aminosalicylate, anhydromethylenecitrate, ascorbate, aspartate, benzoate, benzenesulfonate, bisulfate, bromide, citrate, camphorate, camphorsulfonate, chloride, digluconate, edetate, edisylate, estolate, ethanesulfonate, fumarate, glucoheptanoate, gluconate, glutamate, glycerophosphate, glycolate, hydroxynaphthoate, 2-hydroxyethanesulfonate, iodide, lactate, lactobionate, malate, maleate, mandelate, methylenebis(salicylate), mucate, methanesulfonate, napadisylate, napsylate, pamoate, pantothenate, pectinate, phosphate/diphosphate, polygalacturonate, propionate, salicylate, stearate, succinate, sulfate, tartrate, tosylate and undecanoate. Other anionic species will be apparent to the ordinarily skilled chemist.

The compound of the invention may be used in a variety of pharmaceutical preparations. Compositions for injection, the preferred route of delivery, may be prepared in unit dosage form in ampoules or in multidose containers. The compositions may take such forms as suspensions, solutions or emulsions, oily or aqueous in nature, and may contain various formulating agents, such as diluents, buffers, preservatives and the like. Hence, the compound is present in combination with these pharmaceutically acceptable carriers.

Alternatively, the active ingredient may be in the form of a powder, which can be reconstituted with a suitable carder such as sterile water, normal saline and the like at the time of administration. The powder can be in lyophillized or non-lyophillized form.

Oral compositions are typically in the form of tablets, capsules, solutions or suspensions. Such compositions may likewise be packaged in unit dose or multidose containers. In these oral compositions, the pharmaceutically acceptable carders may be comprised of diluents, tabletting and granulating aids, lubricants, disintegrants, buffers, sweeteners, preservatives and the like.

Topical applications may be formulated with a pharmaceutically acceptable carrier in the form of hydrophobic or hydrophilic ointments, creams, lotions, solutions, paints or powders.

The dosage to be administered depends to a large extent upon the condition and size of the subject being treated as well as the route and frequency of administration. The parenteral route (by injection) is preferred for generalized infections. Such matters, however, are typically left to the discretion of the clinician according to principles of treatment well known in the antibacterial ans.

The compositions for human delivery per unit dosage, whether liquid or solid, may contain from about 0.01% to about 99% of active material, the preferred range being from about 10–60%. The composition will generally contain from about 15 mg to about 2000 mg of the active ingredient; however, in general, it is preferable to employ a dosage amount in the range of from about 250 mg to 1000 mg. In parenteral administration, the unit dosage is usually the compound I in a sterile water or saline solution or in the form of a soluble powder intended for solution.

The preferred method of administration of the compound of formula I is parenterally by intravenous (i.v.) infusion. Alternatively, the compound may be administered intramuscularly (i.m.).

For adults, a dose of about 5 to about 50 mg of the formula I antibacterial compound per kg of body weight is administered from 1 to 6 times per day. The preferred dosage ranges from about 250 mg to 1000 mg of the compound given one to four times per day.

More specifically, for mild infections a dose of 250 mg two to four times daily is preferred. For moderate infections against highly susceptible gram positive organisms a dose of 500 mg b.i.d. to q.i.d. is preferred. For severe, life-threatening infections against organisms at the upper limits of sensitivity to the antibiotic, a dose of about 1000–2000 mg two to six times daily is preferred.

For children, a dose of 5–25 mg/kg of body weight given 1 to 4 times per day is preferred; a dose of 10 mg/kg b.i.d., t.i.d. or q.i.d. is recommended.

The compound of formula I is of the broad class known as carbapenems. Naturally occuring carbapenems are susceptible to attack by a renal enzyme known as dehydropeptidase (DHP). This attack or degradation may reduce the efficacy of the carbapenem antibacterial agent. The compound of the present invention is significantly less subject to such attack, and therefore may not require the use of a DHP inhibitor. However, such use is optional and contemplated to be part of the present invention. Inhibitors of DHP and their use with carbapenem antibacterial agents are disclosed in European Patent Applications No. 79102616.4, filed Jul. 24, 1979 (Patent No. 0 007 614); and No. 82107174.3, filed Aug. 9, 1982 (Publication No. 0 072 014)].

The compound of the present invention may, where DHP inhibition is desired or necessary, be combined or used with the appropriate DHP inhibitor as described in the aforesaid patents and published application. The cited European Patent Application defines the procedure for determining DHP susceptibility of the present carbapenems and disclose suitable inhibitors, combination compositions and methods of treatment.

A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

The compound of the present invention is active against various gram-positive and to a lesser extent gram-negative bacteria, and accordingly find utility in human and veterinary medicine. The compound is a potent anti-MRSA/MRCNS compound.

The compound of the present invention has surprising and unexpected safety benefits in that the dosages which cause seizures in mammals are substantially higher than the dosages of other related carbapenems. To demonstrate, laboratory test animals (rats) are evaluated by counting the seizures induced when the test compound is dissolved in water in different concentrations and applied to brain tissue. Each animal is injected with 20 μl in the intracistemal cavity. Unexpectedly lower CNS (seizure) activity is observed for the compound of the present invention than for other related compounds.

Additionally, the pharmacokinetic profile for the compound of the invention is surprisingly better than that of related compounds. In particular, the half life of the compound is noted to be unexpectedly longer.

The invention is further described in connection with the following non-limiting examples.

EXAMPLE 1

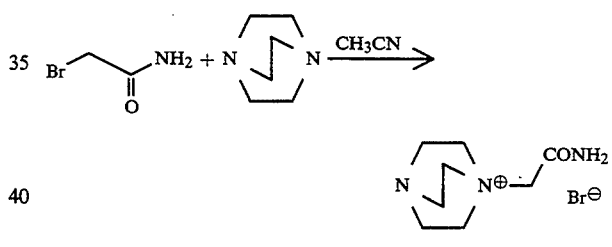

1-(aminocarbonylmethyl)-4-aza-1-azoniabicyclo(2.2.2)octane bromide (1)

To a stirred solution of 1,4-diazabicyclo[2.2.2]octane (17.93 g, 0.1599 mol) in 200 ml of acetonitrile at 0° C. was added dropwise a solution of 2-bromoacetamide (20.05 g, 0.1453 mol) in 200 ml of acetonitrile during 25 min. A precipitate began depositing several minutes into the addition. The milky-white reaction mixture was stirred and allowed to warm to room temperature overnight. After 20 h, the white solid was isolated by filtration, washing with ~200 ml of acetonitrile. Drying in vacuo gave 33.37 g of white solid. This material was combined with product from a previous preparation giving a total of 37.93 g for recrystallization. The solid was dissolved in ~230 ml of boiling ethanol, filtered while hot, and allowed to cool slowly overnight. The solution was seeded while still very warm. The mother liquors were decanted from the dense crystalline mass and the crystals were washed three times with cold ethanol (~50 ml total). Drying in vacuo gave 30.47 g of 1 as large colorless hygroscopic prisms, mp 194°–198° C.

$^1$H-NMR (400 Mz, 2:1 D$_2$O/CD$_3$CN): δ3.48 (t, J=7.5 Hz, 6H), 3.90 (t, J=7.5 Hz, 6H), 4.28 (s, 2H).

EXAMPLE 2

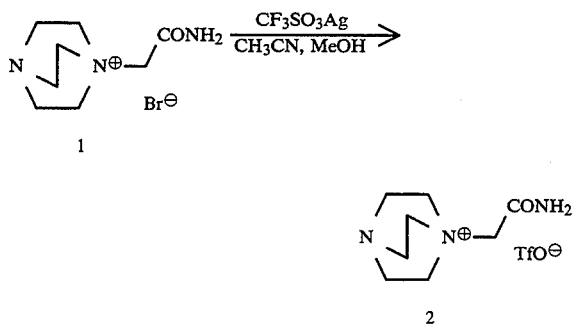

To a stirred solution of the bromide salt 1 (30.43 g, 0.1217 mmol) in methanol at room temperature was added dropwise a solution of silver trifluoromethanesulfonate (29.69 g, 0.1156 mol, 0.95 eq.) in 100 ml of acetonitrile during 20 min. The reaction mixture was protected from light. A precipitate formed immediately and the resulting yellow reaction mixture was stirred for 30 min and then filtered, washing with acetonitrile. The filtrate was evaporated in vacuo to give a white solid which was taken-up in 600 ml of acetonitrile, filtered to remove a small amount of insoluble material and the filtrate evaporated to give 37.1 g of a white solid. The crude solid was recrystallized from ~550 ml of boiling ethanol, allowing the solution to cool to room temperature slowly overnight and seeding while still hot. The mother liquors were decanted from the crystalline mass and the crystals were washed twice with 75 ml of cold ethanol. Drying in vacuo yielded 32.93 g of 2 as white flakes, mp 174°-176° C.

$^1$H-NMR (400 Mz, d$_6$-acetone): δ3.29 (t, J=7.6 Hz, 6H), 3.77 (t, J=7.6 Hz, 6H), 4.20 (s, 2H), 7.1 (bs, 1H), 7.6 (bs, 1H).

EXAMPLE 3

Compound 3A (10.0 g, 25.6 mmol) was dissolved in CH$_2$Cl$_2$ (51 mL) and rhodium(II) octanoate (50 mg) was added. The reaction mixture was heated at reflux for 3 h. Additional CH$_2$Cl$_2$ (77 mL) was added and the reaction was cooled to −78° C. Triethylamine (3.75 mL, 26.9 mmol, 1.05 equiv) was then added dropwise over several minutes and the reaction was stirred for 15 min before trifluoromethanesulfonic anhydride (4.52 mL, 26.9 mmol, 1.05 equiv) was added slowly dropwise. The reaction was stirred an additional 15 min before adding triethylamine (3.93 mL, 28.2 mmol, 1.1 equiv) followed by the addition of triethylsilyl trifluoromethanesulfonate (6.36 mL, 28.2 mmol, 1.1 equiv), both added slowly dropwise. This mixture was then stirred for 75 min at −78° C.

The fluorenone boronic acid 3C (7.15 g, 28.2 mmol, 1.1 equiv) was dissolved in 64 mL of 1-methyl-2-pyrrolidinone and added to the reaction vessel via cannula. Tris(dibenzylideneacetone)dipalladiumchloroform catalyst (53 1 mg, 0.51 mmol, 0.02 equiv) was then added as a solid. A 6N aqueous KOH solution (12.8 mL, 76.8 mmol) was added last. The ice bath was removed and the reaction vessel warmed briefly using a warm water bath before being placed in an oil bath set at 50° C. After approximately 45–50 min the enol triflate intermediate 3B was completely consumed according to TLC (SIO$_2$, 1:1 EtOAc/Hexanes). The contents of the reaction vessel were poured into Et$_2$O and washed with saturated NaHCO$_3$ solution (2×), water/brine mixture [3:1] (5×), and finally brine (2×). The organic layer was treated with decolorizing charcoal for approximately 5 min before MgSO$_4$ was added. Filtration and removal of the solvent in vacuo afforded a wine-red colored foam which was purified via SiO$_2$ Flash Chromatography (EtOAc/Hexanes) to provide 10.36 g of 3.

$^1$H NMR (400 MHz, CDCl$_3$) δ0.61 (q, J=8.05 Hz, 6H), 0.95 (t, J=7.9 Hz, 9H), 1.11 (d, J=7.3 Hz, 6H), 1.28 (d, J=6.2 Hz, 6H), 1.92 (t, J=6.0 Hz, 1H), 3.36 (dd, J=5.9, 3.1 Hz, 1H), 3.40–3.47 (m, 1H), 4.25–4.32 (m,

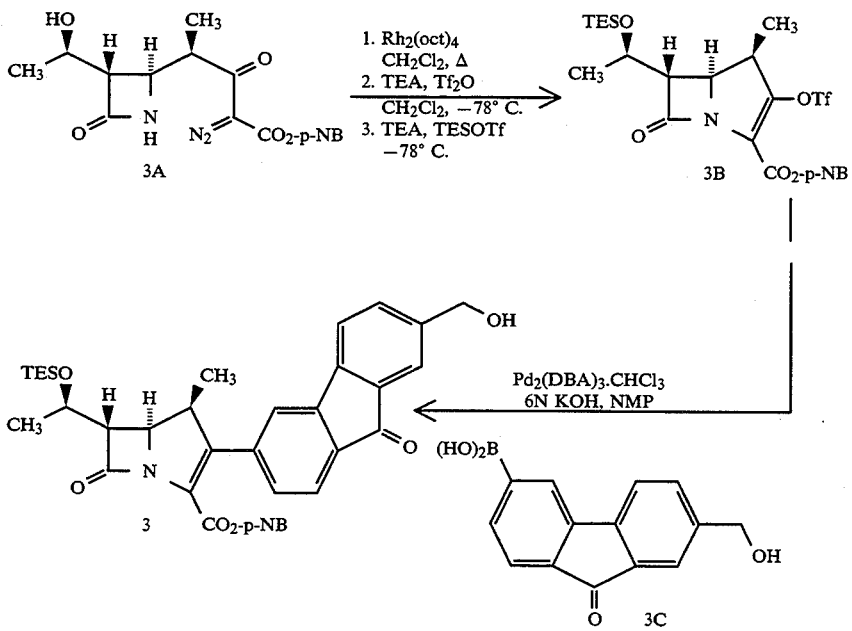

p-Nitrobenzyl (1S,5R,6S)-1-methyl-2-[7-hydroxymethyl-fluoren-9-on-3-yl]-6-(1R-triethylsilyloxyethyl)-carbapen-2-em-3-carboxylate (3)

1H), 4.39 (dd, J=10.2, 3.1 Hz, 1H), 4.70 (d, J=5.5 Hz, 2H), 5.17 (ABq, $J_{AB}$=13.5 Hz, $\Delta v_{AB}$=33.5 Hz, 2H), 7.16 (dd, J=7.6, 1.4 Hz, 1H), 7.28–7.35 (complex m, 4H), 7.45 (dd, J=7.7, 1.5 Hz, 1H), 7.6–7.64 (m, 2H), 7.97 (d, J=8.8 Hz, 2H).

EXAMPLE 4

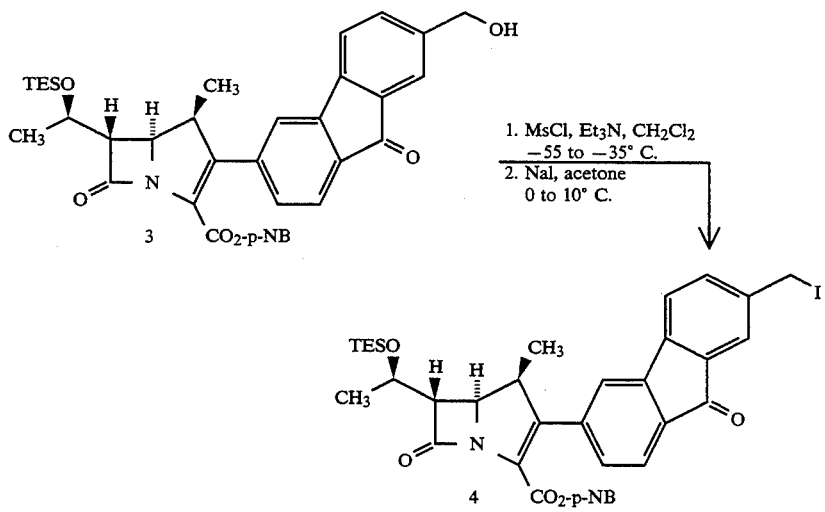

p-Nitrobenzyl (1S, 5R, 6S)-1-methyl-2-[7-iodomethyl-fluoren-9-on-3-yl]-6-(1R-triethylsilyloxyethyl)-carbapen-2-em-3-carboxylate (4)

A solution of the fluorenone-carbinol 3 (20.070 g, 30.008 mmol) in 300 ml of dichloromethane was cooled to −55° C. and triethylamine (6.0 ml, 43 mmol, 1.4 eq.) was added followed by the dropwise addition of methanesulfonyl chloride (2.8 ml, 36 mmol, 1.2 eq.) during several minutes. The reaction temperature was allowed to rise to −35° C. during 55 min at which point TLC (SiO2, 1:4 EtOAc/CH2Cl2) showed no remaining starting material. The reaction mixture was diluted into 1:1 ethyl acetate-diethyl ether and washed successively with water, sat. aqueous ammonium chloride solution, water, and brine. Drying over sodium sulfate, filtration, and evaporation gave the crude mesylate intermediate as a yellow foam which was used immediately without purification.

The crude mesylate was dissolved in 300 ml of acetone, cooled to 0° C., and sodium iodide (9.00 g, 60.0 mmol, 2.0 eq.) was added in one portion with stirring. The reaction mixture was stirred in the dark at 0+ C. for 1 h and then the ice bath was replaced with a 10° C. bath and the stirring was continued for an additional 1 h. At this point TLC (1:1 EtOAc/hexane) showed the reaction to be essentially complete with only a trace of mesylate remaining. The cooling bath was removed and the reaction mixture was stirred for 15 min more and then diluted into 1:1 ethyl acetate-diethyl ether. The organic solution was washed with dilute sodium chloride solution (2×), 5% sodium thiosulfate solution/brine (3:1 ), dilute sodium chloride solution, and brine. The organic layer was dried over sodium sulfate and evaporated in vacuo leaving a slightly gummy yellow solid. The crude iodide was dissolved in 150 ml of benzene and lyophilized to yield 22.720 g of 4 as a fluffy yellow solid which was used without purification.

1H-NMR (400 MHz, CDC3): δ0.61 (q, J=7.8 Hz, 6H), 0.95 (t, J=7.8 Hz, 9H), 1.10 (d, J=7.3 Hz, 3H), 1.28, (d, J=6.2 Hz, 3H), 3.36 (dd, J=5.8, 3.2 Hz, 1H), 3.44 (m, 1H), 4.30 (m, 1H), 4.40 (dd, J=10.3, 3.2 Hz, 1H), 4.45 (s, 3H), 5.13 (d, J=13.5 Hz, 1H), 5.27 (d, J=13.5 Hz, 1H), 7.20 (dd, J=7.6, 1.4 Hz, 1H), 7.32 (d, J=7.5 Hz, 1H), 7.40 (s, 1H), 7.43 (d, J=8.8 Hz, 2H), 7.47 (dd, J=7.7, 1.8 Hz, 1H), 7.63 (d, J=7.7 Hz, 1H), 7.65 (d, J=1.4 Hz, 1H), 8.06 (d, J=8.8 Hz, 2H).

EXAMPLE 5

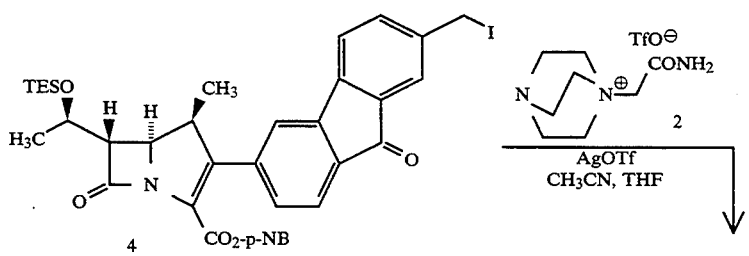

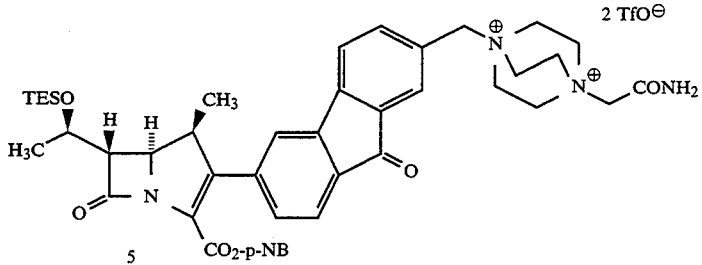

p-Nitrobenzyl (1S,5R,6S)-1-methyl-2-{7-[4-(aminocarbonylmethyl)-1,4-diazoniabicyclo(2.2.2)octan-1-yl]methyl-fluoren-9-on-3-yl}-6-(1R-triethylsilyloxyethyl)-carbapen-2-em-3-carboxylate bis-trifluoromethanesulfonate (5)

The iodide 4 (12.547 g, 16.112 mmol) was dissolved in 290 ml of acetonitrile and 30 ml of tetrahydrofuran with stirring at room temperature. The ammonium trifluoromethanesulfonate salt 2 (5.145 g, 16.11 mmol) was added in one portion as a solid and dissolved within several minutes. A solution of silver trifluoromethanesulfonate in acetonitrile (0.964M, 16.0 ml, 15.4 mmol, 0.957 eq.) was added slowly dropwise with stirring in the dark during 40 min. A precipitate began depositing immediately, and after the addition was complete the reaction mixture was stirred for an additional 35 min. Methanol (30 ml) was added and the reaction mixture was filtered through a pad of Celite®, washing with acetonitrile. The solution was rotary evaporated to low volume and the resulting slurry was dissolved in ~175 ml of 9:1 acetone-methanol. The slightly hazy solution was filtered through a pad of Celite® washing with additional 9:1 acetone-methanol. The total volume of the filtrate was ~250 ml of clear orange solution. The solution was vigorously stirred while 250 ml of diethyl ether was added relatively rapidly from an addition funnel (addition time ~10 min). Precipitation of the product began after ~70 ml of the diethyl ether had been added. After the addition was complete, the mixture was stirred for 5 min more, and then suction filtered through a coarse filter funnel, washing with 300 ml of 2:1 diethyl ether-acetone followed by 300 ml of diethyl ether. The solid was air-dried on the funnel and then in a vacuum desiccator overnight to yield 15.590 g of 5 as a yellow solid.

$^1$H-NMR(400 MHz, d$_6$-acetone): δ50.66(q, J=8.0 Hz, 6H), 0.99(t,J=8.0 Hz, 9H), 1.15 (d, J=7.4 Hz, 3H), 1.28 (d, J=6.2 Hz, 3H), 3.54 (dd, J=4.7, 3.4 Hz, 1H), 3.68 (d, J=13.6 Hz, 1H), 4.37 (m, 1H), 4.44–4.51 (m, 7H), 4.55–4.62 (m, 6H), 4.67, (s, 2H), 5.18 (d, J=13.6 Hz, 1H), 5.20 (s, 2H), 5.29 (d, J=13.6 Hz, 1H), 7.26 (bs, 1H), 7.50 (dd, J=7.6, 1.4 Hz, 1H), 7.55 (d, J=8.8 Hz, 2H), 7.66 (d, J=7.7 Hz, 1H), 7.68 (bs, 1H), 7.86 (s, 1H), 7.89 (d, J=7.3 Hz, 1H), 7.89 (d, J=1.3 Hz, 1H), 7.96 (dd, J=7.9, 1.5 Hz, 1H), 8.02 (d, J=8.8 Hz, 2H).

EXAMPLE 6

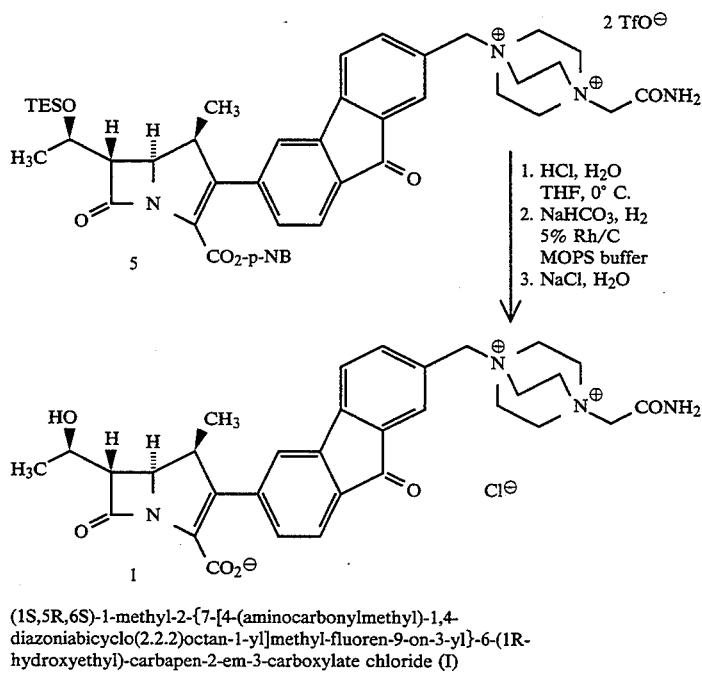

(1S,5R,6S)-1-methyl-2-{7-[4-(aminocarbonylmethyl)-1,4-diazoniabicyclo(2.2.2)octan-1-yl]methyl-fluoren-9-on-3-yl}-6-(1R-hydroxyethyl)-carbapen-2-em-3-carboxylate chloride (I)

Carbapenem 5 (4.50 g; 4.02 mmol) was dissolved in 120 mL of 2:1 THF/H$_2$O and cooled to 0° C. The pH of this solution, which began at 4.86, was adjusted to 2.30 using 1N HCl (3.40 mL; 3.40 mmol; 0.85 equiv). The disappearance of the TES-group was monitored by RP HPLC (LiChrospher 100, RP-18; 85:15 CH$_3$CN/0.10M NH4Cl) and the hydrolysis was judged to be complete after 80 min. The reaction mixture was neutralized to pH 7.0 using 1M NaHCO3 (3.60 mL; 3.60 mmol; 0.90 equiv), and 40 mL of 0.5M pH 6.75 MOPS buffer was added. Ten percent w/w of 5% Rh/C (450 mg) was added and the flask was purged 10 times with H2. The solution was stirred vigorously under balloon pressure of H2 for 80 min at which time the reaction was judged to be complete by RP HPLC (LiChrospher 100, RP-18; 35:65 CH3CN/0.10M NH4Cl). Following removal of the H2, the reaction mixture was filtered through a pad of Celite ® rinsing with 2:1 H2O/CH3CN. The solution was frozen and lyophilized overnight. The crude product was taken-up in 20% aqueous NaCl, filtered through Celite ® and purified by MPLC through a column packed with Amberchrom ® CG-162sd resin to yield 1.631 g of I as a fluffy orange solid UV (H2O): $\lambda_{max}$32 368 nm.

1H-NMR (400 MHz, 2:1 D2O/CD3CN): δ1.42 (d, J=7.2 Hz, 3H), 1.60 (d, J=6.2 Hz, 3H), 3.77 (dd, J=5.9, 2.7 Hz, 1H), 3.85 (m, 1H), 4.23–4.35 (m, 6H), 4.43–4.55 (m, 6H), 4.54 (m, 1H), 4.62 (s, 2H), 4.64 (dd, partially obscured, 1H), 5.05 (s, 2H), 7.79 (d, J=8.0 Hz, 1H), 7.94 (d, J=7.7 Hz, 1H), 7.98 (s, 1H), 8.01 (d, J=7.7 Hz, 1H), 8.11 (d, J=8.0 Hz, 1H), 8.13 (s, 1H).

What is claimed is:

1. A compound represented by the formula I:

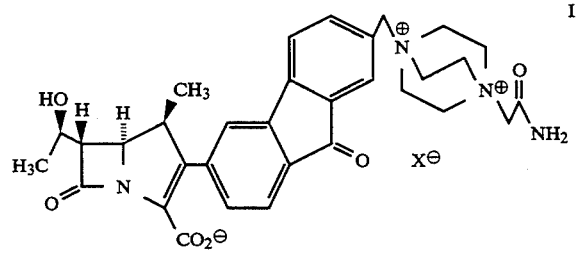

wherein $X^{\ominus}$ represents a negatively charged counterion.

2. A compound in accordance with claim 1 wherein $X^{\ominus}$ represents a member selected from the group consisting of acetate, adipate, aminosalicylate, anhydromethylenecitrate, ascorbate, aspartate, benzoate, benzenesulfonate, bisulfate, bromide, citrate, camphorate, camphorsulfonate, chloride, digluconate, edetate, edisylate, estolate, ethanesulfonate, fumarate, glucoheptanoate, gluconate, glutamate, glycerophosphate, glycolate, hydroxynaphthoate, 2-hydroxyethanesulfonate, iodide, lactate, lactobionate, malate, maleate, mandelate, methylenebis(salicylate), mucate, methanesulfonate, napadisylate, napsylate, pamoate, pantothenate, pectinate, phosphate, diphosphate, polygalacturonate, propionate, salicylate, stearate, succinate, sulfate, tartrate, tosylate and undecanoate.

3. A compound in accordance with claim 2 wherein $X^{\ominus}$ represents chloride.

4. A pharmaceutical composition comprised of a compound as defined in claim 1 in combination with a pharmaceutically acceptable carrier.

5. A pharmaceutical composition in accordance with claim 4 further comprised of a DHP inhibitor.

6. A pharmaceutical composition in accordance with claim 5 wherein the DHP inhibitor is 7-(L-2-amino-2-carboxyethylthio)-2-(2,2-dimethylcyclopropanecarboxamide)-2-heptenoic acid.

7. A pharmaceutical composition in accordance with claim 4 wherein $X^{\ominus}$ represents a member selected from the group consisting of acetate, adipate, aminosalicylate, anhydromethylenecitrate, ascorbate, aspartate, benzoate, benzenesulfonate, bisulfate, bromide, citrate, camphorate, camphorsulfonate, chloride, digluconate, edetate, edisylate, estolate, ethanesulfonate, fumarate, glucoheptanoate, gluconate, glutamate, glycerophosphate, glycolate, hydroxynaphthoate, 2-hydroxyethanesulfonate, iodide, lactate, lactobionate, malate, maleate, mandelate, methylenebis(salicylate), mucate, methanesulfonate, napadisylate, napsylate, pamoate, pantothenate, pectinate, phosphate, diphosphate, polygalacturonate, propionate, salicylate, stearate, succinate, sulfate, tartrate, tosylate and undecanoate.

8. A pharmaceutical composition in accordance with claim 7 wherein $X^{\ominus}$ represents chloride.

9. A pharmaceutical composition in accordance with claim 7 further comprised of a DHP inhibitor.

10. A pharmaceutical composition in accordance with claim 9 wherein the DHP inhibitor is 7-(L-2-amino-2-carboxyethylthio)-2-(2,2-dimethylcyclopropanecarboxamide)-2-heptenoic acid.

11. A pharmaceutical composition in accordance with claim 8 further comprised of a DHP inhibitor.

12. A pharmaceutical composition in accordance with claim 11 wherein the DHP inhibitor is 7-(L-2-amino-2-carboxyethylthio)-2-(2,2-dimethylcyclopropanecarboxamide)-2-heptenoic acid.

13. A method of treating a bacterial infection in a mammal in need of such treatment, comprising administering to said mammal a compound as defined in claim 1 in an amount which is effective for treating said bacterial infection.

14. A method of treating a bacterial infection in a mammal in need of such treatment, comprising administering to said mammal a compound as defined in claim 2 in an amount which is effective for treating said bacterial infection.

15. A method of treating a bacterial infection in a mammal in need of such treatment, comprising administering to said mammal a compound as defined in claim 3 in an amount which is effective for treating said bacterial infection.

16. A method of treating a bacterial infection in accordance with claim 13, further comprising administering to said mammal a DHP inhibitor.

17. A method of treating a bacterial infection in accordance with claim 16 wherein the DHP inhibitor is 7-(L-2-amino-2-carboxyethylthio)-2-(2,2-dimethylcyclopropanecarboxamide)-2-heptenoic acid.

18. A method of treating a bacterial infection in accordance with claim 14, further comprising administering to said mammal a DHP inhibitor.

19. A method of treating a bacterial infection in accordance with claim 15 further comprising administering to said mammal a DHP inhibitor.

20. A method of treating a bacterial infection in accordance with claim 18 wherein the DHP inhibitor is 7-(L-2-amino-2-carboxyethylthio)-2-(2,2-dimethylcyclopropanecarboxamide)-2-heptenoic acid.

21. A method of treating a bacterial infection in accordance with claim 19 wherein the DHP inhibitor is 7-(L-2-amino-2-carboxyethylthio)-2-(2,2-dimethylcyclopropanecarboxamide)-2-heptenoic acid.

* * * * *